United States Patent
Sugano et al.

(10) Patent No.: US 9,128,018 B2
(45) Date of Patent: Sep. 8, 2015

(54) METHOD FOR EVALUATING CORROSION-FATIGUE LIFE OF STEEL MATERIAL

(71) Applicant: HITACHI METALS, LTD., Tokyo (JP)

(72) Inventors: Ryuuichiroh Sugano, Shimane (JP); Hidemitsu Horie, Shimane (JP); Kouta Kataoka, Shimane (JP); Yousuke Nakano, Shimane (JP)

(73) Assignee: HITACHI METALS, LTD., Tokyo (JP)

( * ) Notice: Subject to any disclaimer, the term of this patent is extended or adjusted under 35 U.S.C. 154(b) by 0 days.

(21) Appl. No.: 14/205,876

(22) Filed: Mar. 12, 2014

(65) Prior Publication Data

US 2014/0283619 A1    Sep. 25, 2014

(30) Foreign Application Priority Data

Mar. 19, 2013 (JP) .................... 2013-056084

(51) Int. Cl.
   *G01N 3/32* (2006.01)
   *G01N 17/00* (2006.01)

(52) U.S. Cl.
   CPC ............... *G01N 17/006* (2013.01); *G01N 3/32* (2013.01); *G01N 2203/0005* (2013.01); *G01N 2203/0066* (2013.01); *G01N 2203/0075* (2013.01); *G01N 2203/024* (2013.01)

(58) Field of Classification Search
   CPC ............. G01N 2203/0066; G01N 2203/027; G01N 3/32
   USPC ........................................... 73/799
   See application file for complete search history.

(56) References Cited

U.S. PATENT DOCUMENTS

2007/0169563 A1 * 7/2007 Hohjo et al. ............... 73/799

FOREIGN PATENT DOCUMENTS

| EP | 2352007 A1 | 8/2011 |
|----|------------|--------|
| JP | S48-075086 A | 10/1973 |
| JP | S63-088739 U | 6/1988 |
| JP | 2010-107372 A | 5/2010 |

* cited by examiner

*Primary Examiner* — Lisa Caputo
*Assistant Examiner* — Nathaniel T Woodward
(74) *Attorney, Agent, or Firm* — Greenblum & Bernstein, P.L.C.

(57) ABSTRACT

A method for evaluating the corrosion-fatigue life of a steel material includes: bringing a corrosive medium into contact with a predetermined portion of the steel material; measuring strain on the steel material while applying cyclic loads to the steel material; measuring an N-th strain index from strain amplitude at the number of initial load applications and strain amplitude at the N-th load application (N is a natural number larger than the number of initial load applications); and estimating the corrosion-fatigue life of the steel material by comparing the N-th strain index with a previously certified life strain index.

16 Claims, 4 Drawing Sheets

METHOD FOR EVALUATING CORROSION-FATIGUE LIFE OF STEEL MATERIAL

CROSS-REFERENCE TO RELATED APPLICATION

This application claims priority from Japanese Patent Application No. 2013-056084 filed with the Japan Patent Office on Mar. 19, 2013, the entire content of which is hereby incorporated by reference.

BACKGROUND

1. Technical Field

The present disclosure relates to a method for evaluating corrosion-fatigue properties of steel materials used under corrosive environment.

2. Related Art

Generally, the corrosion-fatigue life of a steel material is evaluated as the time when a crack is generated in a predetermined portion that is in contact with a corrosive medium under cyclic loading. For example, the number of crack generation cycles is measured as a numerical index for evaluating the life. In a strict sense, the "number of crack generation cycles" is defined as follows: If cyclic loads are applied to a steel material under corrosive environment, a crack is generated in the steel material. The number of cyclic load applications (the number of cycles) at the time of crack generation in the steel material is referred to as the "number of crack generation cycles".

Procedures used for the evaluation are described in, for example, patent documents JP-A-2010-107372, JP-A-48-075086, and JP-U-63-088739. The method described in JP-A-2010-107372, cyclic loads are applied to the surface of a test specimen having a corrosive medium introduced into a space formed inside the test specimen. The corrosion-fatigue damage is then evaluated. JP-A-48-075086 proposes a corrosive liquid tank for conducting a fatigue test under corrosive atmosphere. A columnar fatigue test specimen is attached to the corrosive liquid tank. A loading mode is axial force. Moreover, JP-U-63-088739 proposes a stress corrosion cracking test apparatus. This apparatus includes means for applying a tensile load to a test specimen based on a measured stress value by a strain gauge. In the corrosion-fatigue test, cyclic loads are applied to a test specimen under the environment of a corrosive medium. In the measurement of the number of crack generation cycles, generally, the corrosion-fatigue test is conducted two or more times to improve the reliability of the measured values. The number of crack generation cycles is obtained as, for example, the average value of the plurality of obtained measured values.

SUMMARY

A method for evaluating the corrosion-fatigue life of a steel material includes: bringing a corrosive medium into contact with a predetermined portion of the steel material; measuring strain on the steel material while applying cyclic loads to the steel material; measuring an N-th strain index from strain amplitude at the number of initial load applications and strain amplitude at the N-th load application (N is a natural number larger than the number of initial load applications); and estimating the corrosion-fatigue life of the steel material by comparing the N-th strain index with a previously certified life strain index.

DETAILED DESCRIPTION

Figure 1:
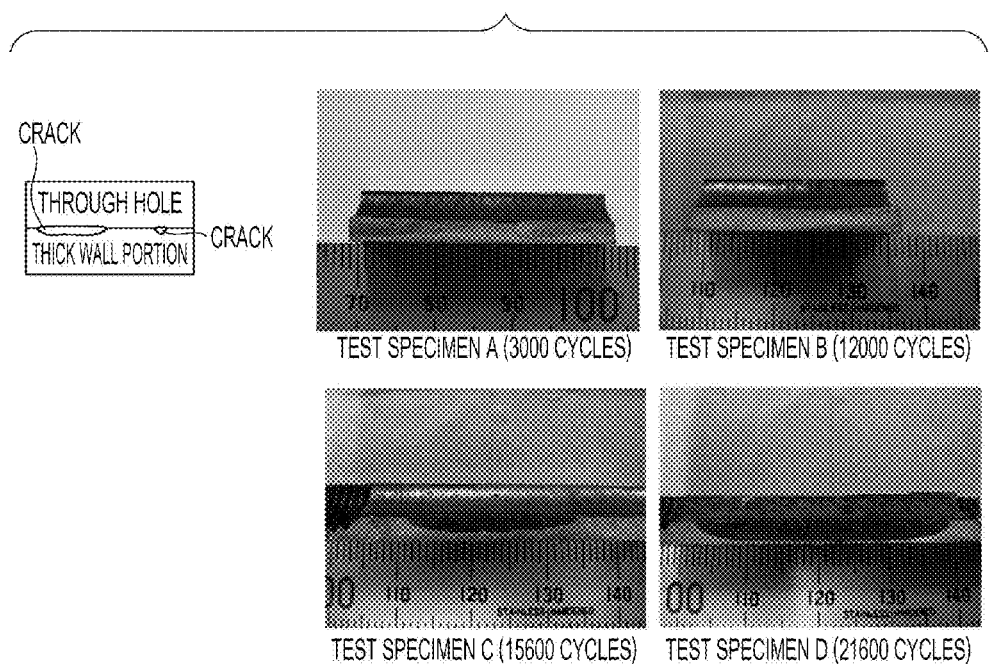
FIG. 1 is a photographic representation as a substitute for a drawing, illustrating fracture surfaces obtained by applying cyclic loads to test specimens each including an internal space where a corrosive medium has been introduced and then breaking the test specimens, and illustrates examples of the situation of corrosion fatigue that has occurred in the internal spaces.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Out of JP-A-2010-107372, JP-A-48-075086, and JP-U-63-088739, the method of JP-A-2010-107372 uses, as a test specimen, a steel material including an internal space where a corrosive medium has been introduced. In other words, the method can apply cyclic loads to a surface of the test specimen using an existing simple fatigue test apparatus. However, for example, if the number of crack generation cycles is obtained to evaluate the corrosion-fatigue life of a steel material in the method of JP-A-2010-107372, the surface and/or cross section of the test specimen are observed after a predetermined number of repetitive load cycles. The number of crack generation cycles is determined by a "direct correlation" from the observed state of the test specimen. Therefore, when there is a difference in the evaluation criterion (in other words, individual sense) of a damage form between measurers on the spot, a big error may occur in the identified number of crack generation cycles even if the test conditions are the same. Conducting the test two or more times may also cause differences in a plurality of the obtained numbers of crack generation cycles. Hence, the number of crack generation cycles obtained by simply averaging a plurality of results is low in reliability. Therefore, such a method may invite discrepancies in life evaluation.

An object of the present disclosure is to provide a method that makes it possible to obtain the corrosion-fatigue life of a steel material in a corrosion-fatigue test with high reliability.

In the conventional evaluation methods, the observed state of a corroded portion of a test specimen, which can vary depending on decisions on the spot, is set as an evaluation criterion, and a corrosion-fatigue life is determined directly from the evaluation criterion. As the evaluation criterion of a corrosion-fatigue life of a steel material instead of the conventional evaluation criterion, the present inventors have investigated the use of a novel evaluation criterion, which hardly cause a difference depending on a test time and/or a measurer. As a consequence, the present inventors have found that the use of the value of a "strain index" is appropriate. The "strain index" can be obtained by processing the value of a strain generated on a test specimen during testing under predetermined conditions. The value of the "strain index" is an absolute evaluation criterion, which can be obtained as a mathematical value. Furthermore, the present inventors have finally found that "the strain index" exhibits a substantially fixed value proper to each test specimen when cracking begins to occur. Before a corrosion-fatigue test (the test) is conducted on an evaluation test specimen whose corrosion-fatigue life is desired to be evaluated, for example, a corrosion-fatigue test (the preliminary test) is conducted on preliminary test specimens. The preliminary test makes it possible to know in advance the strain index of the evaluation test specimen when cracking begins to occur (that is, the life strain index). In the test, the corrosion-fatigue life (the number of crack generation cycles) of the evaluation test specimen can be estimated by comparing the measured strain index to the value of the life strain index. Therefore, the present inventors have found that the method enables the accurate evaluation of a corrosion-fatigue life.

In other words, a method for evaluating the corrosion-fatigue life of a steel material according to an embodiment of the present disclosure (the evaluation method) includes:

bringing a corrosive medium into contact with a predetermined portion of the steel material;

measuring strain on the steel material while applying cyclic loads to the steel material;

measuring an N-th strain index from strain amplitude at the number of initial load applications and strain amplitude at the N-th load application (N is a natural number larger than the number of initial load applications); and estimating the corrosion-fatigue life of the steel material by comparing the N-th strain index with a previously certified life strain index.

The evaluation method may further include introducing the corrosive medium into an internal space of the steel material, and placing a strain measuring device on an outside of the steel material. Furthermore, in the evaluation method, the strain may be measured by a strain gauge.

The evaluation method may include:

bringing a corrosive medium into contact with a predetermined portion of the steel material;

measuring strain on the steel material while applying cyclic loads to the steel material;

measuring an N-th strain index from strain amplitude at the number of initial load applications and strain amplitude at the N-th load application (N is a natural number larger than the number of initial load applications);

checking the presence or absence of a crack in the portion of the steel material after the N-th load application, the portion being in contact with the corrosive medium;

setting, as a temporary life strain index, the N-th strain index when a crack is observed;

measuring the temporary life strain indexes of a plurality of steel materials; and determining the previously certified life strain index based on the plurality of the temporary life strain indexes.

If the crack cannot be observed, the number of load applications may be increased until crack generation can be observed. The presence or absence of the crack may be observed by destructive testing.

According to the evaluation method, the evaluation of a life with few errors, for example, the estimation of the number of crack generation cycles can be performed in a series of steps of a corrosion-fatigue test. In the evaluation method, the evaluation of the life of a steel material and the estimation of the number of crack generation cycles can be performed by, for example, conducting a preliminary test, even if a damage form of a test specimen is not observed in the test. Consequently, it is possible to obtain substantially accurate corrosion-fatigue properties of steel materials used under corrosive environment, for example, various dies for die casting or plastic molding, and machine components even if a test performer changes. Therefore, the evaluation method can be a useful method for the standardization of evaluation methods.

Hereinafter, an evaluation method according to an embodiment of the present disclosure will be described.

The evaluation method uses a "strain index" as an evaluation criterion indicating that a steel material under a corrosion-fatigue test has reached the end of its corrosion-fatigue life. The "strain index" is measured from the value of a strain generated on a test specimen under the test. The strain index is an index measured from strain amplitude $\Delta_{\epsilon 0}$ and strain amplitude $\Delta_{\epsilon}$. The strain amplitude $\Delta_{\epsilon 0}$ is the amplitude of strain at the number of initial load applications in the test specimen. The strain amplitude $\Delta_{\epsilon}$ is the amplitude of strain at the N-th load application (N is a natural number that is larger than the number of initial load applications). The strain index is, for example, a value calculated by performing subtraction or division between the values of $\Delta_{\epsilon 0}$ and $\Delta_{\epsilon}$. An example thereof is a difference in the strain amplitudes ($\Delta_{\epsilon} - \Delta_{\epsilon 0}$). The value of a strain index at the N-th load application (the "N-th strain index") exhibits a substantially fixed value between test specimens when cracking begins to occur in the test specimens. Therefore, the N-th strain index when the cracking begins to occur can be found in advance by, for example, conducting the preliminary test. Consequently, a life with few errors, for example the number of crack generation cycles, can be estimated without increasing the number of times of the test to improve the accuracy of the obtained number of crack generation cycles as in the case of the prior art, or further checking a fatigue damage surface of a test specimen after the test.

Figure 5:
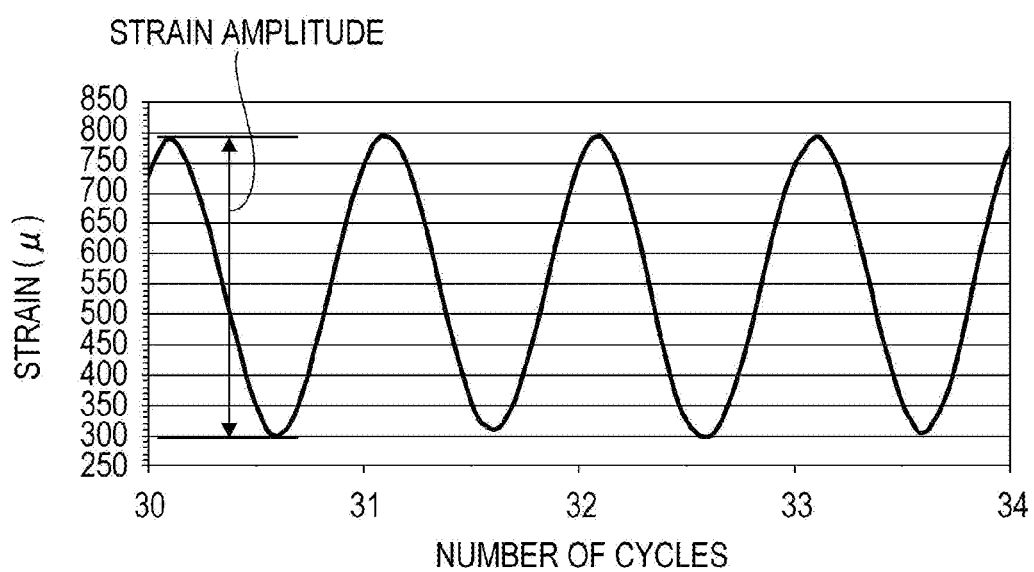
FIG. 5 is a graph illustrating an example of changes in strain generated on the test specimen under cyclic loading.

In the corrosion-fatigue test, when cyclic loads are applied to a steel material under testing, strain occurs on a predetermined portion of the steel material. The strain includes predetermined amplitude in accordance with the number of repetitive cycles (that is, the number of load applications) (FIG. 5). The strain amplitude varies depending on differences in factors such as the kind of the steel material (the quality of the material, the hardness thereof, and the like), and the value of a load to be applied. In one corrosion-fatigue test where the factors are respectively fixed, while the number of repetitive cycles is low, strain amplitude is substantially constant even if the number of repetitive cycles increases. The substantially constant strain amplitude corresponds to the strain amplitude $\Delta_{\epsilon 0}$ at the number of initial load applications. If the number of repetitive cycles (the number of load applications) further increases, a crack is generated in the predetermined portion. If the crack is generated, the strain $\Delta_{\epsilon 0}$ having the substantially constant amplitude increases to the value of $\Delta_{\epsilon}$. From this point on, the strain $\Delta_{\epsilon}$ increases with the growth of the crack. The inventors found a constant law contained in such a relationship between the growth of a crack and an increase in strain.

The "number of initial load applications" is the number of applications in the early period of the test before strain shows an increasing tendency, or, in short, the number of load applications in the initial stage of the test. However, the relationship between the number of load applications (the number of repetitive cycles) and the amount of strain may not be stable immediately after the start of the test and becomes substantially constant after the number of repetitive cycles increases up to a point. Therefore, the time when the relationship between the number of load applications and strain is stabilized and becomes substantially constant as described above may be set as "initial." Strain amplitude at the number of the "initial" load cycles may be set to $\Delta_{\epsilon 0}$. The range of the number of "initial" cycles at which strain becomes substantially constant is, for example, 2000 to 2500 cycles.

In other words, the strain value varies depending on the differences in the factors such as the kind of the steel material and/or a load to be applied. The inventors found the following points on the value of the strain index. In other words, the value of a strain index obtained by processing the strain value in accordance with a definition such as the above ($\Delta_\epsilon - \Delta_{\epsilon 0}$) is substantially the same regardless of the differences in the factors. The value of the strain index becomes substantially constant after, for example, the number of load applications exceeds the number of initial load applications. The value of the strain index is substantially constant even if the number of repetitive cycles increases. However, the value of the strain index shows an increasing tendency after cracking begins to occur in the predetermined portion. Furthermore, the value of the strain index increases with the growth of the crack (FIG. 4; the values on the vertical axis are strain indexes by the above ($\Delta_\epsilon - \Delta_{\epsilon 0}$). The value of the strain index at the time when the increasing tendency is indicated is also substantially the same regardless of the differences in the factors. The value of the strain index at the time when the increasing tendency is indicated can be certified as, for example, a strain index when the cracking begins to occur (that is, the life strain index) by a method such as a preliminary test to be described below. Therefore, the life strain index is certified in advance before the test on a steel material whose corrosion-fatigue life is desired to be evaluated is conducted. Consequently, the value of the N-th strain index during the measurement of the steel material under the test is compared to the previously certified life strain index to enable easy estimation of the corrosion-fatigue life of the steel material in the test.

The methods for estimating a corrosion-fatigue life by comparison include the following. For example, the time when the N-th strain index in the test exceeds the life strain index can be estimated to be the corrosion-fatigue life of the steel material. Alternatively, a constant safety factor for the life or the rounding (round-off or the like) of the index within a range without serious inconvenience can also be adopted. In this case, the time when the N-th strain index exceeds an index that is slightly lower or higher than the life strain index may be estimated to be the corrosion-fatigue life of the steel material. The number of load applications ("N-th time") at that point in time may be estimated to be the number of crack generation cycles. If the safety factor or rounding is adopted, the number of cycles that is slightly lower or higher than the "N-th" load applications may be estimated to be the number of crack generation cycles.

In the evaluation method, upon the evaluation of the corrosion-fatigue life of a steel material, a corrosive environment may be formed (placed) outside the steel material or formed inside the steel material. Specifically, if the corrosive environment is formed inside the steel material, the steel material to be evaluated by the evaluation method may be a steel material including an internal space where a corrosive medium has been introduced, as described in JP-A-2010-107372. In this case, cyclic loads that work directly on a surface of the steel material can be applied to the steel material, using an existing simple fatigue test machine. The "surface of the steel material" to which the cyclic loads are applied is, for example, an outer surface of the steel material, and is the outer surface opposed to the internal space, the outer surface being in contact with the corrosive medium via the thick wall of the steel material.

In the evaluation method, an object to be measured is set as a steel material including an internal space where a corrosive medium has been introduced and accordingly strain generated on the steel material during the corrosion-fatigue test can easily be measured at low cost. If the steel material is in the corrosive medium, strain on the steel material is generally measured in a non-contact manner. The measurement is performed by using, for example, an optical method such as laser. Hence, a measuring apparatus is expensive and complicated. In this respect, in a case of the steel material including the internal space where the corrosive medium has been introduced, a strain measuring device can be placed outside the steel material. In other words, for example, strain can be measured while the strain measuring device is in contact with the outer surface of the steel material. In other words, an inexpensive and easy method can be used. The strain measuring device may be a strain gauge.

The strain gauge is used to measure strain by an electrical resistance strain gauge. The electrical resistance strain gauge uses a phenomenon where the electrical resistance of a resistant material including metal changes due to strain on the resistant material. The strain gauge including the resistant material is attached to, for example, the outer surface of a steel material being an object to be measured. Consequently, the same strain as that of the steel material occurs on the strain gauge during testing. The strain is detected as a change in electrical resistance. The method is easy and inexpensive. The strain gauge is lightweight and also good in responsiveness, and also appropriate for dynamic strain measurement. When the strain gauge is attached, the direction of the gauge length may be oriented in the direction in which cyclic loads are applied. In this case, the amount of change in strain can be detected more accurately. For example, a difference between the direction in which cyclic loads are applied and the direction in which the strain gauge is attached may be within a range of ±3°.

Hereinafter, the evaluation method will be described in detail using one specific example.

<First Step> A test specimen being a steel material including an internal space where a corrosive medium has been introduced and a strain measuring device on its outside is prepared.

The requirements are as described above. The steel material is set as the test specimen including the internal space where the corrosive medium has been introduced. Consequently, cyclic loads working directly on the surface of the specimen can be applied to the surface of the test specimen using an existing simple fatigue test machine. Moreover, strain can be measured from the outside of the test specimen. Hence, measurement can be performed using an inexpensive and easy method. A strain measuring device may be a strain gauge.

<Second Step> Strains on the test specimen are measured by the strain measuring device while cyclic loads are being applied to the test specimen. The N-th strain index is measured from strain amplitude at the number of initial load applications and strain amplitude at the N-th load application (N is a natural number that is larger than the number of initial load applications).

An evaluation criterion in the evaluation method is a strain that occurs on the test specimen in agreement with the time when the life of the test specimen during the corrosion-fatigue test ends. Therefore, in the second step of the evaluation method, for example, strains that occur on the test specimen from the beginning to the N-th load application through the initial stage where strain becomes stable are measured over the entire test. For example, the N-th strain index that is defined as the difference between the above ($\Delta_\epsilon - \Delta_{\epsilon 0}$) can be obtained from a plurality of strain values obtained by these measurements.

<Third Step> The N-th strain index is compared with a previously certified life strain index. Consequently, the corrosion-fatigue life of the steel material is estimated.

In the evaluation method, for example, the preliminary test, which is described below, is conducted. Consequently, an appropriate life strain index in agreement with the time when cracking begins to occur in the internal space of the test specimen where the corrosive medium has been introduced can be certified in advance. Therefore, when the value of the strain index of the steel material under measurement reaches the N-th load application during the test, the value of the N-th strain index is compared with the value of the previously certified life strain index. From the comparison result, the corrosion-fatigue life of the steel material can easily be estimated using the above-mentioned procedure and the like. The number of crack generation cycles can be estimated from the number of load applications at that point in time ("N-th time") using the above-mentioned procedure and the like.

Next, a method for determining the previously certified life strain index (that is, the preliminary test) will be described.

In the preliminary test, the life strain index is determined. The concept of the procedure of the preliminary test is the same as that of the test. In other words, also in the preliminary test, a corrosive medium is brought into contact with a predetermined portion of a steel material. In this state, while cyclic loads are being applied to the steel material, strains on the steel material are measured. The N-th strain index is measured from strain amplitude at the number of initial load applications and strain amplitude at the N-th load application (N is a natural number that is larger than the number of initial load applications). The presence or absence of a crack in the portion of the steel material, the portion being in contact with the corrosive medium, is checked after the N-th load application. The life strain index is determined based on the N-th strain index when a crack is observed. The index "when a crack is observed" may be determined based on, for example, the actual level (length, area, and the like) of the crack.

However, even if the strain index measured in the preliminary test is an index in accordance with the N-th load application where cracking occurs, the crack may be determined whether or not to be in the initiation stage. Therefore, a plurality of strain index values that change (increase) with increasing degree of crack growth may be collected. Consequently, the life strain index can be certified from the plurality of strain indexes measured at the N-th time. This is effective for the determination of the accurate time when the corrosion-fatigue life is exhausted. The presence or absence of cracks in steel materials is checked to collect the plurality of strain indexes measured at the N-th time, for example, whenever cracking occurs in the steel material (or also at the point when cracking has not yet occurred). In other words, a plurality of steel materials may be prepared for the preliminary test. In other words, in the preliminary test of the evaluation method, the presence or absence of a crack in the portion of the steel material, the portion being in contact with the corrosive medium, is checked after the N-th load application. The N-th strain index when a crack is observed is set to be a "temporary" life strain index. The temporary life strain indexes of the plurality of steel materials are measured. The previously certified life strain index is determined based on a plurality of the temporary life strain indexes. The life strain index certified by this method is effective as the evaluation criterion used for the evaluation of the corrosion-fatigue life of a steel material, the evaluation criterion allowing the estimation of a highly reliable corrosion-fatigue life.

The term "based on the plurality of the temporary life strain indexes" upon the determination of the previously certified life strain index will be described. For example, it is possible to set, as the previously certified life strain index, the temporary life strain index measured at the N-th time that is the lowest count out of the plurality of the temporary life strain indexes. Alternatively, an average value of the plurality of the temporary life strain indexes may be calculated or the index may be rounded (rounded off, or the like) within a range without serious inconvenience depending on the constant safety factor for the life, or the like. An index that is slightly lower or higher than the value of the temporary life strain index measured at the N-th time that is the lowest count can also be set as the previously certified life strain index as a result of operating the index in this manner.

Moreover, if a crack cannot be observed in the work of checking the presence or absence of a crack in the steel material, a check on the crack can be repeated again by increasing the number of load applications until crack generation can be observed. In this case, a method for observing the portion in contact with the corrosive medium can be used for a check on the presence or absence of a crack by a method without breaking the steel material (for example, a method using a microscope). However, generally, a crack grows from a surface of the portion toward the depth direction. Hence, after the presence or absence of a crack is checked, the steel material may be broken to accurately determine whether or not the crack is in the initiation stage (that is, a crack at the time when the corrosion-fatigue life was exhausted) or whether or not the crack has largely grown from the initial stage (that is, a crack after the corrosion-fatigue life was exhausted). In other words, a plurality of steel materials may be prepared to check the presence or absence (or kind) of cracks in the steel materials by destructive testing. Furthermore, the steel material may be broken so as to expose a cross section including the crack and accordingly its fracture surface may be observed. As a breaking method, a method that does not crush a minute crack may be used. For example, the steel material may be forced to be broken by applying a load to the steel material by a servo-hydraulic testing machine or the like after dividing the steel material into two on a vertical plane to the load application direction (FIG. 1).

In the preliminary test, intermediate strain indexes up to the N-th strain index at the time of crack generation in the steel material, and strain indexes after N cycles may also be measured. Based on the measurement results, a relationship diagram between the numbers of cyclic load applications and the measured strain indexes may be created.

Figure 4:
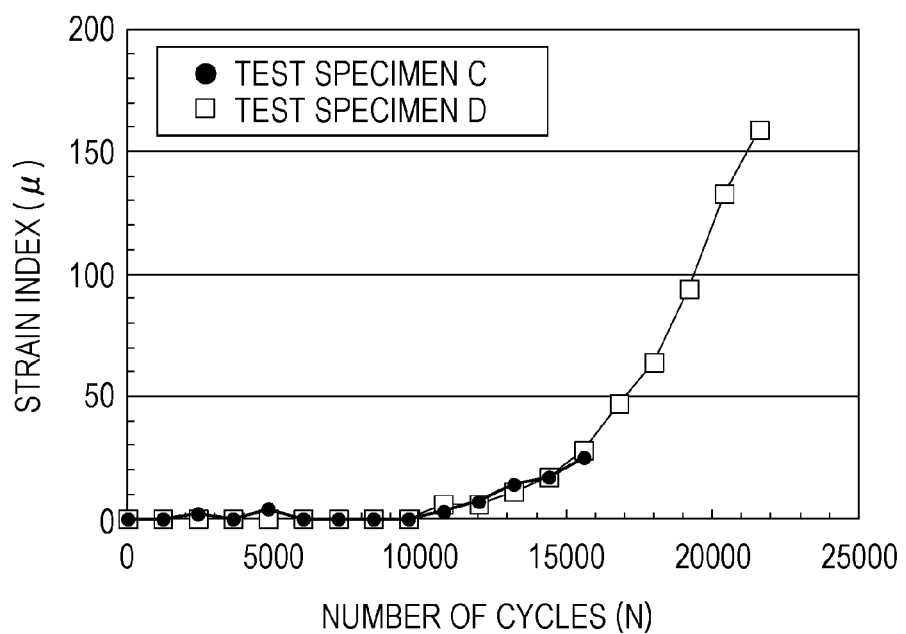
FIG. 4 is a graph illustrating an example of relationships between the numbers of load cycles on test specimens and measured strain indexes.

The inventors found that the strain index measured on a steel material during the corrosion-fatigue test and the number of cyclic load applications indicates a continuous correlation. The inventors then determined that the strain indexes measured continuously indicate a substantially constant value in the stage where a crack is not generated in the steel material (the initial stage of the test) and that the strain index shows an increasing tendency after the number of load applications increases and a crack is generated in the steel material (FIG. 4). Strictly speaking, the strain index at the time of starting to indicate the increasing tendency corresponds to the life strain index. This phenomenon is considered to be caused as follows. If a crack is generated in the internal space of the steel material, the thickness (thick wall) of the steel material between the internal space and the outer surface of the steel material where the strain measuring device is placed becomes thin. Hence, even if a load at the same strength is applied, the amount of deformation (strain) of the steel material increases.

Hence, a relationship diagram of the "numbers of cyclic load applications—strain indexes" over the entire test may be created. Consequently, it is possible to visually confirm that the number of cyclic load applications corresponding to the vicinity of a point of increase (a point of inflection) of the strain index in the relationship diagram serves as one index of the number of crack generation cycles estimated in the subsequent test. Therefore, the relationship diagram may be standardized among a plurality of measurers. Consequently, for example, the relationship diagram is referenced in the test to further improve the accuracy and validity of the estimated number of crack generation cycles. Specifically speaking, the method for evaluating the corrosion-fatigue life of a steel material is as follows. Firstly, the relationship diagram is created. The strain index at the time when the strain index starts to increase is obtained from the relationship diagram. Based on the strain index, the previously certified life strain index is determined. In other words, the method may include the following. Firstly, the relationship diagram is created. The number of load applications at which the strain index starts to increase is subsequently obtained from the relationship diagram. Based on the number of load applications, the corrosion-fatigue life of the steel material is estimated.

In the previous section, the inventors described that the strain index values are substantially the same regardless of differences in factors such as the kind of steel material and/or the value of a load (the strength of a load) to be applied. The inventors observed the following fact. In other words, if a crack in a steel material at the time of crack generation in the steel material is, for example, a dot crack in a test specimen B of FIG. 1, which is described below, the strain index (that is, the life strain index) measured at that point in time is a value obtained by the above ($\Delta_\epsilon - \Delta_{\epsilon 0}$) and is within a range of approximately 5 to 15μ (approximately 10μ). "μ" stands for "$10^{-6}$". However, the state (index) of the crack at the time of crack generation in the steel material can be changed to an appropriate one as occasion demands. For example, a (initial) crack that is smaller than the crack in the test specimen B may be applied as the state (index) of the crack at the time of crack generation in the steel material. In this case, the strain index (life strain index) measured at the time of crack generation in the steel material can be less than 5μ by the above ($\Delta_\epsilon - \Delta_{\epsilon 0}$). Moreover, the surface skin of the predetermined portion (internal space) of the steel material, the portion being in contact with the corrosive medium, may be processed smoothly by, for example, polishing. In this case, stresses working on the predetermined portion tend to concentrate on the crack during testing. Hence, in this case, a strain that initiates a crack in a state at the same level as the crack in the test specimen B can be small. In other words, the life strain index can be less than 5μ by the above ($\Delta_\epsilon - \Delta_{\epsilon 0}$). The crack index and/or the degree of processing on the surface skin may be determined in accordance with the level of the corrosion-fatigue properties required for a steel material, the use of the steel material, the accuracy of a strain measuring device, and the like.

Hereinafter, a description will be given of a specific example of the method for determining the life strain index in the evaluation method.

<Step I> A test specimen being a steel material including an internal space where a corrosive medium has been introduced and a strain measuring device on its outside is prepared.

As described in JP-A-2010-107372, a corrosive environment may be formed inside a test specimen used for the evaluation of the corrosion-fatigue life of a steel material. The details have already been described. Step I is similar to, for example, the first step according to the evaluation method.

<Step II> Strains on the test specimen are measured by the strain measuring device while cyclic loads are being applied to the test specimen. The N-th strain index is measured from strain amplitude at the number of initial load applications and strain amplitude at the N-th load application (N is a natural number that is larger than the number of initial load applications).

In the specific example, the life strain index may be certified in advance before the test (the first to third steps) is conducted. The life strain index may be certified by the preliminary test. In other words, in the preliminary test, the level of the strain index measured on the test specimen, where a crack is generated in the test specimen, is checked. Consequently, the life strain index can be certified in advance. Strains that occur on the test specimen until N-th load applications may be measured for the check over the entire preliminary test. The strain index value may be, for example, a value of the N-th strain index as defined by the difference in the above ($\Delta_\epsilon - \Delta_{\epsilon 0}$).

In Step II, intermediate strain indexes up to the N-th strain index at the time of crack generation in the steel material, and strain indexes after the N-th strain index may also be measured. Based on the measurement results, a relationship diagram between the numbers of cyclic load applications and the measured strain indexes may be created.

The details have already been described. Step II may be similar to, for example, the second step according to the evaluation method. In other words, in addition to knowing in advance the N-th strain index (life strain index) at the time of crack generation in the test specimen, intermediate strain indexes up to the N-th strain index and strain indexes after the N-th strain index may also be measured. Consequently, it is possible to know in advance a relationship diagram of the "numbers of cyclic load applications—strain indexes" over the entire test. Consequently, the accuracy and validity of the number of crack generation cycles estimated in the test for corrosion fatigue are further improved.

<Step III> The presence or absence of crack generation in the internal space of the test specimen, where the corrosive medium has been introduced, is checked after N-th load applications.

If the preliminary test for certifying the life strain index is conducted, crack generation in the internal space of the test specimen after a predetermined number of load applications, the internal space having the corrosive medium introduced thereinto, is observed to certify a strain (life strain) at the time of crack generation in the test specimen. If the crack observed at N-th load applications is in the initiation stage (see the test specimen B of FIG. 1), the strain index measured at that point in time includes high validity as the life strain index. Corrosion fatigue occurring in a steel material is a phenomenon where destruction advances with corrosion. The corrosion that has occurred on the surface of the steel material under the corrosive environment progresses, and is generally recognized as a dot crack in the initial stage. Hence, in a steel material observation index, the point in time when a crack similarly to the one formed in the test specimen B of FIG. 1 is formed can be certified as the corrosion-fatigue life of the steel material.

For example, the method for observing the surface of the internal space of a steel material by a microscope or the like can be used to check the presence or absence of a crack. Alternatively, the presence or absence, or kind of a crack may be checked by breaking the test specimen so as to expose a cross section (fracture surface) including the crack and observing the fracture surface (FIG. 1). If the inspection by destruction is used for the work of checking crack generation, a test specimen is broken at every check. Hence, a plurality of test specimens may be prepared.

Moreover, in Steps II and III, the number of cyclic load applications may be changed according to the plurality of test specimens. The remaining work on the plurality of test specimens after loading may simultaneously be performed all together. In other words, a plurality of test specimens is prepared. The number of cycles where cyclic loads are applied to them is determined so as to vary depending on the test specimen. Step IV and later, which are described below, are performed all together on individual test specimens after a predetermined number of load applications (individual test specimens after the corrosion-fatigue test). Consequently, the need to check crack generation at every test is eliminated. Hence, the corrosion-fatigue life can speedily be evaluated. Moreover, the corrosion-fatigue test may be performed on the plurality of test specimens beforehand or at the same time. Afterward, the work of checking crack generation in the test specimens may be performed at the same time. Consequently, the performance environment such as temperature, moisture, and a handling manner by a performer can be standardized between the tests and works. As a consequence, an error in evaluation results can be reduced.

<Step IV> Based on the N-th strain index in the test specimen where crack generation could be observed, the previously certified life strain index is determined.

In Steps II and III, the N-th strain index is measured from the test specimen. That a crack has been generated in the internal space of the test specimen, where the corrosive medium has been introduced, and that the crack "is in the initiation stage" are observed to determine the life strain index from the N-th strain index. If a crack is not observed in the internal space of the test specimen after a predetermined number of load applications, the number of load applications is increased until crack generation can be observed (for example, until a crack at the level indicated in the test specimen B of FIG. 1 can be observed) to conduct the corrosion-fatigue test. Alternatively, further, if a plurality of test specimens where crack generation has been observed can be obtained, for example, the N-th strain index of the test specimen having the lowest number of cyclic load applications among them can be determined to be the life strain index. Alternatively, an index that is slightly lower or higher than the value of the N-th strain index of the test specimen having the lowest number of cyclic load applications can also be set as the life strain index as a result of operating the values of the plurality of the N-th strain indexes as described in the previous section.

As described above, the method for determining the life strain index by Steps I to IV (the preliminary test) may be performed before the first to third steps (the test) are performed. Consequently, the life strain index of a test specimen can be grasped before the test. There is a continuous correlation between the number of cyclic load applications and the strain index (FIG. 4). Moreover, the life strain index of each test specimen is also substantially fixed. Therefore, in the test, the strain index measured on the test specimen under cyclic loading is compared with the life strain index. Consequently, the corrosion-fatigue life of the test specimen can easily be estimated. Based on the number of load applications at this point in time ("N cycles"), the number of crack generation cycles can easily be estimated.

According to the present disclosure, the corrosion-fatigue life (the number of crack generation cycles) of a steel material can easily be estimated with high accuracy without increasing the number of times of the test for corrosion fatigue, or further actually checking the presence or absence of crack generation in the test specimen after the test. An absolute numerical value, a strain index, is set as the evaluation criterion. Hence, it is possible to share the life evaluation result having the same understanding among a plurality of measures. The values of the strain indexes are substantially the same regardless of differences in factors such as the kind of steel material and the value of a load to be applied. On this basis, even if test conditions (the quality of the material of a test specimen, the hardness thereof, the value of a load to be applied, and the like) are different between the preliminary test and the test, it is possible to share a "previously certified life strain index" having the same value. Hence, the acceleration of the evaluation of corrosion-fatigue lives of various steel materials can be expected.

First Example

In the example, assuming an actual die for plastic molding, corrosion-fatigue damage that can be caused in its cooling hole was reproduced to evaluate the corrosion-fatigue life of a steel material used for the die.

Determination of Life Strain Index

<Step I>

Figure 3:
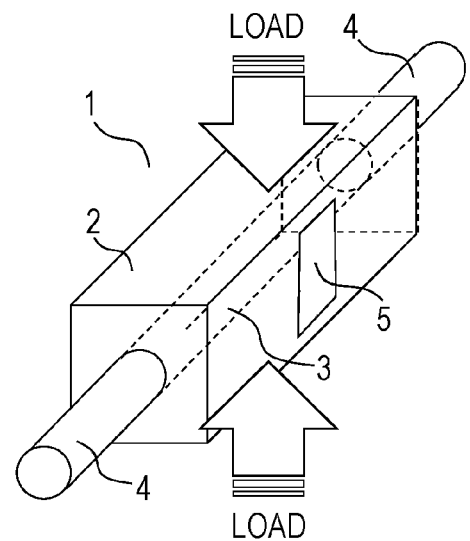
FIG. 3 is a schematic drawing illustrating the appearance of a test specimen used in an example of the present disclosure.

A test specimen 1 illustrated in FIG. 3 was prepared as the test specimen according to the example. The test specimen 1 includes a material piece 2 of a size having a 15 mm square cross section×60 mm in length, and a through hole 3 having a diameter of approximately 10 mm. The through hole 3 is an internal space, provided in the center of the cross section of the material piece 2, for introducing a corrosive medium thereinto. The through hole 3 was formed in a length direction. The through hole 3 was formed by drilling. Joints 4 for continuously allowing the corrosive medium to pass through were attached at both ends of the through hole 3. A strain gauge 5 was placed (attached) to the outer surface of the material piece 2. The strain gauge 5 is a measuring device for strains at the times when cyclic loads are applied to the test specimen 1. The strain gauge 5 was attached to the outer surface of the material piece 2 such that a load application direction agreed with the gauge's longitudinal direction (so as to be within a range of ±3°). The material of the material piece 2 is an improved steel material of SUS420J2 being the kind of steel material of JIS. The material piece 2 was tempered after hardened at 1020° C. Consequently, the hardness of the material piece 2 was adjusted to HRC 50.

<Step II>

3.5% NaCl solution was flown as a corrosive medium through the through hole 3 of the test specimen 1. The preliminary test for corrosion fatigue was conducted in accordance with the form of FIG. 3. In the preliminary test, cyclic loads were applied to two opposing outer surfaces of the test specimen 1 at the same time and at the same strength. These two outer surfaces are two outer surfaces that are opposed to the internal space in contact with the corrosive medium, via the thick wall of the test specimen 1. An unillustrated servo-hydraulic testing machine was used for applying cyclic loads.

The conditions of cyclic loading in the preliminary test were set such that the frequency of cycles was 2 Hz and the maximum primary stress working on a surface of the internal space was a tensile stress of approximately 900 Mpa. Four test specimens A to D made of the test specimen 1 were prepared. Preliminary tests A to D were conducted on the test specimens A to D for the following four numbers of cyclic load applications under the above conditions of the preliminary test. Consequently, the four test specimens A to D on which the preliminary test had been conducted were obtained.

Test A: 3000 cycles
Test B: 12000 cycles
Test C: 15600 cycles
Test D: 21600 cycles During the preliminary test, the strain gauge 5 and an unillustrated electrical resistance strain gauge continuously measured strains in the cyclic load direction, which occurred at the stain gauge attached portion. The strain amplitude became stable at $\Delta_{\epsilon0}$. The strain indexes obtained by the difference ($\Delta_{\epsilon}-\Delta_{\epsilon0}$) between $\Delta_{\epsilon0}$ and the strain amplitude $\Delta_{\epsilon}$ at the last load cycle (at the end of the test) were as follows ("$\mu$" indicates "$10^{-6}$"):

Test A: 0μ
Test B: 10μ
Test C: 25μ
Test D: 159μ

Moreover, data on the strain indexes continuously measured, the data including the above results, was used to create relationship diagrams between the numbers of cyclic load applications (the number of cycles) and the measured strain indexes. FIG. 4 is the above relationship diagrams of the preliminary tests on the test specimens C (15600 cycles) and D (21600 cycles). It can be seen that the curves indicating both of the relationship diagrams substantially agree with each other and that the strain index and the number of cycles exhibit a continuous correlation. The values of the strain indexes exhibit a substantially constant numerical value in the initial stages of the tests and indicate the increasing tendency after the passage of a certain the number of cycles.

<Steps III and IV>

Figure 2:
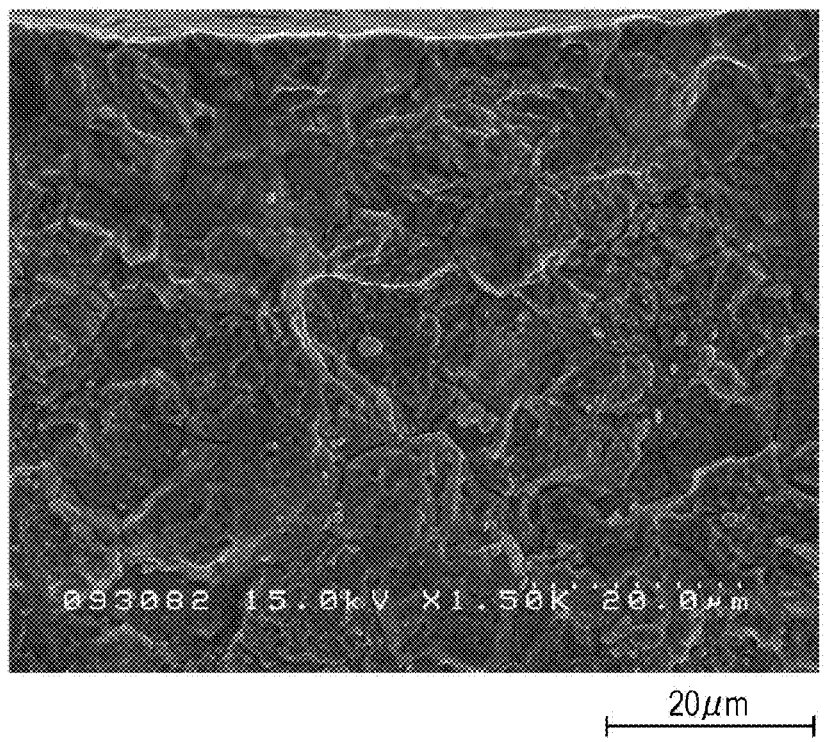
FIG. 2 is a metal micrograph obtained by observing a region where corrosion fatigue has occurred, the region being illustrated in FIG. 1, by a scanning electron microscope.

The four test specimens A to D on which the test were conducted in Step II were broken so as to expose their cross sections that could include cracks, using the servo-hydraulic testing machine. The fracture surfaces were then observed. The fracture surfaces were illustrated in FIG. 1. Corrosion fatigue regions (illustrated in FIG. 1 as dark gray regions compared with thick wall portions) where a crack has grown from the surface to the deep depth (the outer surface of the thick wall portion) of the internal space and where the color had been changed into brown were observed on the fracture surfaces of the test specimens B to D. The fact that these discolored regions were formed due to corrosion fatigue can be observed by, for example, observing the regions with a scanning electron microscope and confirming that the regions show the form of an intergranular fracture with corrosion (FIG. 2 illustrates the observation result of the region of the test specimen B). In terms of the cracks in these corrosion fatigue regions, the crack is an initial dot crack in the test specimen B. In the test specimens C and D, the cracks further grew with an increasing number of load applications. Hence, the discolored regions are slim and their areas are large. In the example, out of the strain indexes at the end of the test (that is, the temporary life strain indexes) in the test specimens B to D where crack generation had been observed, the strain index (10μ) at the end of the test in the test specimen B having the lowest number of load applications was certified in advance as the life strain index of the test specimen.

Furthermore, the above result of the previously certified life strain index was checked against the relationship diagrams between the number of cycles and the strain indexes illustrated in FIG. 4. As a consequence, the value, 10μ, of the life strain index that had been certified in advance substantially agreed with the vicinity of the number of cycles at which the strain index transitions to the increasing tendency in FIG. 4. Therefore, the relationship diagrams of FIG. 4 are standardized and accordingly the result of the estimated life strain index can be visually observed. The result is used to evaluate the corrosion-fatigue life of a steel material and accordingly improvements in the accuracy and validity of the corrosion-fatigue life can be expected.

Evaluation of Corrosion-Fatigue Life

Another test specimen whose corrosion-fatigue life was desired to be known, the test specimen being similar to the test specimens prepared upon the determination of the life strain index, was prepared. The corrosion-fatigue test (the test) was conducted on the test specimen on the same conditions as those of the preliminary test. The number of cyclic load applications was increased and the test was ended when the strain index exceeded the life strain index value of 10μ. The number of load applications at this point in time was 11600. Therefore, in the example, the number of load applications, 11600, was estimated to be the number of crack generation cycles of the test specimen. In order to evaluate the accuracy of the estimation, the test specimen after the test was broken in the same procedure as the above and its fracture surface was observed. As a consequence, an initial dot crack at the same level of the crack that was formed in the test specimen B upon the determination of the life strain index was observed. Consequently, it was observed that the estimation was correct.

Second Example

Determination of Life Strain Index

Figure 6:
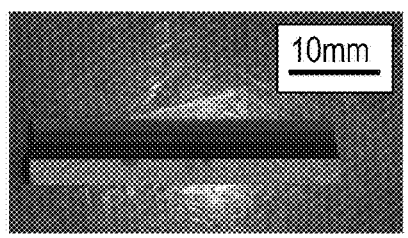
FIG. 6 is a photographic representation as a substitute for a drawing, illustrating a fracture surface obtained by applying cyclic loads to a test specimen including an internal space where a corrosive medium has been introduced and then breaking the test specimen, and illustrates an example of the situation of corrosion fatigue that has occurred in the internal space.

A plurality of test specimens whose kind (the quality of the material, the hardness thereof) had been changed from the test specimens prepared in the first example was prepared. The material of the test specimens is SKD61, the kind of steel material of JIS, used for a die casting mold and the like, and its hardness is HRC 43. Through holes were formed by drilling and polishing the surface skins after processing. Next, the preliminary test for corrosion fatigue was conducted on these test specimens. The conditions of the preliminary test were the same conditions as the first example, except for the setting where the maximum primary stress working on the surface of the internal space was a tensile stress of approximately 600 Mpa. As a result of the preliminary test, cracks were observed on the fracture surfaces of the plurality of test specimens to which cyclic loads had been applied for 96000 cycles and more. The level of the crack in the test specimen to which the cyclic loads were applied for 96000 cycles was a dot at the same level as that of the test specimen B (the fracture surface is illustrated in FIG. 6). The strain index of the test specimen by the above ($\Delta_{\epsilon}-\Delta_{\epsilon0}$) was 3μ. From the above, in the example, out of the strain indexes (that is, the temporary life strain indexes) in the test specimens where crack generation had been observed, the strain index (3μ) of the test specimen having the lowest number of load applications was certified in advance as the life strain index of the test specimen. The life strain index (3μ) of the second example is different from the life strain index (10μ) of the first example. The reason is that in the first example the internal space for introducing the corrosive medium thereinto was formed as the through hole that had been left as it is after drilling, while in the second example the internal space was formed by polishing the surface skin after drilling. Hence, the surface state to come into contact with the corrosive medium may be set to be equal between the test and the preliminary test in order to effectively use the life strain index previously certified in the test.

Evaluation of Corrosion-Fatigue Life

Various test specimens having different qualities of materials and hardness were prepared as test specimens whose corrosion-fatigue lives were desired to be evaluated. These test specimens have a similar shape to the test specimens used in the preliminary test and a through hole. The corrosion-fatigue test was conducted on these various test specimens by applying cyclic loads of the maximum primary stress (tensile stress) different from that on the preliminary test. During the corrosion-fatigue test, the strain index by the above ($\Delta_\epsilon - \Delta_{\epsilon 0}$) was measured while cyclic loads were being applied. When the strain index reached 3μ, the test was ended. The fracture surface of the test specimen on which the test had been ended was observed. The kind of test specimen, the set value of the maximum primary stress, and the number of cyclic load applications (the number of cycles) at which the strain index reached 3μ are illustrated in Table 1.

TABLE 1

| Test specimen | | Maximum primary stress of cyclic loads (MPa) | The number of cycles (N) at which strain index reached 3μ |
|---|---|---|---|
| Quality of Material | Hardness | | |
| SKD61 | HRC 43 | 700 | 86674 |
| | | 850 | 14680 |
| | | 1000 | 10382 |
| | HRC 45 | 600 | 55884 |
| | | 700 | 45490 |
| | | 850 | 32298 |
| | | 1000 | 19212 |
| Improved steel material of SUS420J2 | HRC 44 | 900 | 33840 |
| | HRC 54 | 900 | 15712 |

The number of cyclic load applications (strict corrosion-fatigue life) at which the strain index reached 3μ varies depending on the kind of test specimen and the condition of applying cyclic loads. It was observed that the higher the strength of an applied load was, the smaller the number of cyclic load applications at the end of the corrosion-fatigue life was. This is a normal tendency of a general corrosion-fatigue test result. Even if the numbers of cyclic load applications of the test specimens at the end of the corrosion-fatigue life are different from each other, the level of cracks observed on the fracture surfaces of the test specimens at the end of the corrosion-fatigue lives was equal to the level of the crack in the test specimen of the preliminary test (FIG. 6). From the above, it was found that the corrosion-fatigue lives of various steel materials can be evaluated by sharing a "previously certified life strain index" having the same value even if the kinds of test specimen and/or values of loads to be applied (load strengths) are different between the preliminary test and the test.

The present disclosure can also be applied to the evaluation of the corrosion-fatigue lives of steel materials used for, for example, a die casting mold, a bolt of a structure, and a machine component, in addition to a steel material used for a die for plastic molding.

The strain index may be an index measured from the strain amplitude $\Delta_{\epsilon 0}$ at the time of applying an initial load to a test specimen and the strain amplitude $\Delta_\epsilon$ at the time of occasionally applying loads until the N-th load application (N is a natural number larger than the number of initial load applications) after the application of the initial load. Moreover, it can also be said that the strain index value (and a relationship between a load and the amount of strain) transitions with a substantially constant value after the application of the initial load.

If the strain index value at the time when the increasing tendency is indicated can be certified by, for example, a method of the preliminary test, which is described below, to be the strain index when the cracking begins to occur (that is, the life strain index), a life strain index is certified in advance before the test is conducted on a steel material whose corrosion-fatigue life is desired to be evaluated. Accordingly, it is possible to easily estimate the corrosion-fatigue life of the steel material in the test by comparing the value of the N-th strain index under the measurement of the steel material during the test and the previously certified life strain index.

The technology of the present disclosure may do an evaluation, setting, as an evaluation criterion, a strain generated on a test specimen when the test specimen during the corrosion-fatigue test reached the end of its life.

Whenever cracking occurs in the steel material (or also when cracking has not yet occurred), the work of checking the presence or absence of cracks in the steel materials at that point in time may be performed to collect a plurality of strain indexes measured at the N-th time.

The "initial load" is a load at the number of load cycles before strain shows an increasing tendency not long after the start of the test, and may simply be the first load to be applied in the test. However, a relationship between a load and the amount of strain may not be stable immediately after the start of the test and transition substantially constantly after the number of repetitive cycles increases up to a point. Therefore, the time when the relationship between a load and strain becomes stable and substantially constant as described above may be set as "initial" and strain amplitude at the time of the application of the "initial" load may be handled as $\Delta_{\epsilon 0}$.

In the present disclosure, before the first to third steps (the test) were performed, the method for determining a life strain index by Steps I to IV (the preliminary test) was performed and accordingly, the life strain index of the test specimen has been grasped. When the number of load applications was increased, the strain indexes had continuous correlations with increasing load cycles (FIG. 4) and the life strain index was also almost fixed between the test specimens. Therefore, in the test, it is possible to easily estimate the corrosion-fatigue life of the test specimen by comparing the strain index measured on the test specimen under cyclic loading with the above life strain index. The number of crack generation cycles can be easily estimated based on the number of load cycles, N-th time, at this point in time.

In the present disclosure, even if the number of times of the test for corrosion fatigue on a steel material whose corrosion-fatigue life is desired to be evaluated is not increased to improve the accuracy of the obtained corrosion-fatigue life (the number of crack generation cycles), or further, the presence or absence of crack generation in the test specimen after the test is not actually checked, the life can easily be estimated. Since an absolute numerical value of a strain index is set as an evaluation criterion, it is possible to share a life evaluation result having the same understanding among a plurality of measures. Considering that the strain index values are substantially the same regardless of differences in factors such as the kind of steel material and the value of a load to be applied, even if test conditions (the quality of the material of a test specimen, its hardness, the value of a load to be applied, and the like) are different between the preliminary test and the test, a "previously certified life strain index" with the same value can be shared and accordingly the acceleration of the evaluation of the corrosion-fatigue lives of various steel materials can be expected.

Moreover, the method for evaluating the corrosion-fatigue life of a steel material of the present disclosure may be the following first to sixth evaluation methods. The first evaluation method is a method for evaluating the corrosion-fatigue life of a steel material, and includes applying cyclic loads in a state where a corrosive medium is in contact with a predetermined portion of the steel material while measuring strain on the steel material, measuring an N-th strain index from strain amplitude at the number of initial load applications and strain amplitude at the N-th load application (N is a natural number that is larger than the number of initial load applications), and comparing the N-th strain index and a previously certified life strain index and estimating the corrosion-fatigue life of the steel material.

The second evaluation method according to the first evaluation method includes that the corrosive medium has been introduced into an internal space of the steel material, and the steel material has strain measuring means on its outside.

The third evaluation method according to the first or second evaluation method includes that the means for measuring strain is a strain gauge.

The fourth evaluation method according to any of the first to third evaluation methods includes applying cyclic loads in a state where the corrosive medium is in contact with the predetermined portion of the steel material while measuring strain on the steel material, measuring the N-th strain index from the strain amplitude at the number of initial load applications and the strain amplitude at the N-th load application (N is a natural number that is larger than the number of initial load applications), checking the presence or absence of a crack in the portion of the steel material, the portion being in contact with the corrosive medium, after the N-th load application, setting the N-th strain index when a crack is observed as a temporary life strain index, measuring the temporary life strain indexes using a plurality of steel materials, and determining the previously certified life strain index based on the plurality of the temporary life strain indexes.

In the fifth evaluation method according to the fourth evaluation method, when the crack cannot be observed, the number of load applications is increased until crack generation can be observed and the check on a crack is repeated.

In the sixth evaluation method according to the fourth evaluation method, the check on the presence or absence of the crack includes a check by destructive testing.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A method for evaluating the corrosion-fatigue life of a steel material comprising:
    bringing a corrosive medium into contact with a predetermined portion of the steel material;
    measuring a strain amplitude on the steel material while applying cyclic loads to the steel material;
    measuring an N-th strain index from the strain amplitude at the number of initial load applications through which the strain amplitude is substantially constant and from the strain amplitude at the N-th load application (N is a natural number larger than the number of initial load applications); and
    estimating the corrosion-fatigue life of the steel material by determining the value of N for which the strain index value reaches or exceeds a value equal to a previously certified life strain index.

2. The method for evaluating the corrosion-fatigue life of a steel material according to claim 1, further comprising:
    introducing the corrosive medium into an internal space of the steel material; and
    placing a strain measuring device on an outside of the steel material.

3. The method for evaluating the corrosion-fatigue life of a steel material according to claim 2, wherein the strain is measured by a strain gauge.

4. The method for evaluating the corrosion-fatigue life of a steel material according to claim 2, further comprising:
    bringing a corrosive medium into contact with a predetermined portion of the steel material;
    measuring a strain amplitude on the steel material while applying cyclic loads to the steel material;
    measuring an N-th strain index from the strain amplitude at the number of initial load applications through which the strain amplitude is substantially constant and from the strain amplitude at the N-th load application (N is a natural number larger than the number of initial load applications);
    checking the presence or absence of a crack in the portion of the steel material after the N-th load application, the portion being in contact with the corrosive medium;
    setting, as a temporary life strain index, the N-th strain index when a crack is observed;
    measuring the temporary life strain indexes of a plurality of steel materials that includes one of a plurality of identical steel materials and a plurality of different variations of steel materials; and
    determining the previously certified life strain index based on the plurality of the temporary life strain indexes.

5. The method for evaluating the corrosion-fatigue life of a steel material according to claim 4, further comprising increasing the number of load applications until crack generation is observed, when the crack is not observed.

6. The method for evaluating the corrosion-fatigue life of a steel material according to claim 4, comprising checking the presence or absence of the crack by destructive testing.

7. The method for evaluating the corrosion-fatigue life of a steel material according to claim 3, further comprising:
    bringing a corrosive medium into contact with a predetermined portion of the steel material;
    measuring a strain amplitude on the steel material while applying cyclic loads to the steel material;
    measuring an N-th strain index from the strain amplitude at the number of initial load applications through which the strain amplitude is substantially constant and from the strain amplitude at the N-th load application (N is a natural number larger than the number of initial load applications);
    checking the presence or absence of a crack in the portion of the steel material after the N-th load application, the portion being in contact with the corrosive medium;

setting, as a temporary life strain index, the N-th strain index when a crack is observed;

measuring the temporary life strain indexes of a plurality of steel materials that includes one of a plurality of identical steel materials and a plurality of different variations of steel materials; and determining the previously certified life strain index based on the plurality of the temporary life strain indexes.

8. The method for evaluating the corrosion-fatigue life of a steel material according to claim 7, further comprising increasing the number of load applications until crack generation is observed, when the crack is not observed.

9. The method for evaluating the corrosion-fatigue life of a steel material according to claim 7, comprising checking the presence or absence of the crack by destructive testing.

10. The method for evaluating the corrosion-fatigue life of a steel material according to claim 1, wherein the strain is measured by a strain gauge.

11. The method for evaluating the corrosion-fatigue life of a steel material according to claim 10, further comprising:

bringing a corrosive medium into contact with a predetermined portion of the steel material;

measuring a strain amplitude on the steel material while applying cyclic loads to the steel material;

measuring an N-th strain index from the strain amplitude at the number of initial load applications through which the strain amplitude is substantially constant and from the strain amplitude at the N-th load application (N is a natural number larger than the number of initial load applications);

checking the presence or absence of a crack in the portion of the steel material after the N-th load application, the portion being in contact with the corrosive medium;

setting, as a temporary life strain index, the N-th strain index when a crack is observed;

measuring the temporary life strain indexes of a plurality of steel materials that includes one of a plurality of identical steel materials and a plurality of different variations of steel materials; and determining the previously certified life strain index based on the plurality of the temporary life strain indexes.

12. The method for evaluating the corrosion-fatigue life of a steel material according to claim 11, further comprising increasing the number of load applications until crack generation is observed, when the crack is not observed.

13. The method for evaluating the corrosion-fatigue life of a steel material according to claim 11, comprising checking the presence or absence of the crack by destructive testing.

14. The method for evaluating the corrosion-fatigue life of a steel material according to claim 1, further comprising:

bringing a corrosive medium into contact with a predetermined portion of the steel material;

measuring a strain amplitude on the steel material while applying cyclic loads to the steel material;

measuring an N-th strain index from the strain amplitude at the number of initial load applications through which the strain amplitude is substantially constant and from the strain amplitude at the N-th load application (N is a natural number larger than the number of initial load applications);

checking the presence or absence of a crack in the portion of the steel material after the N-th load application, the portion being in contact with the corrosive medium;

setting, as a temporary life strain index, the N-th strain index when a crack is observed;

measuring the temporary life strain indexes of a plurality of steel materials that includes one of a plurality of identical steel materials and a plurality of different variations of steel materials; and determining the previously certified life strain index based on the plurality of the temporary life strain indexes.

15. The method for evaluating the corrosion-fatigue life of a steel material according to claim 14, further comprising increasing the number of load applications until crack generation is observed, when the crack is not observed.

16. The method for evaluating the corrosion-fatigue life of a steel material according to claim 14, comprising checking the presence or absence of the crack by destructive testing.

* * * * *